(12) United States Patent
Smith

(10) Patent No.: US 8,790,406 B1
(45) Date of Patent: Jul. 29, 2014

(54) SYSTEMS AND METHODS FOR PERFORMING SPINE SURGERY

(76) Inventor: William D. Smith, Las Vegas, NV (US)

( * ) Notice: Subject to any disclaimer, the term of this patent is extended or adjusted under 35 U.S.C. 154(b) by 125 days.

(21) Appl. No.: 13/437,917

(22) Filed: Apr. 2, 2012

Related U.S. Application Data

(60) Provisional application No. 61/471,069, filed on Apr. 1, 2011.

(51) Int. Cl.
*A61F 2/44* (2006.01)

(52) U.S. Cl.
USPC ......... 623/17.16; 606/279; 600/202; 600/546

(58) Field of Classification Search
CPC .............. A61B 5/04001; A61B 5/0488; A61B 5/4893; A61B 5/0492; A61B 5/743; A61B 5/1106; A61B 5/7217; A61B 2017/00022; A61B 2017/00039; A61N 1/08
USPC ............ 623/17.11, 17.16; 600/202, 210, 213, 600/215, 184, 214, 219, 235, 546, 554, 600/547; 606/90, 129, 190, 191, 198, 279, 606/32, 41; 607/43, 2, 131, 130
See application file for complete search history.

(56) References Cited

U.S. PATENT DOCUMENTS

| | | | |
|---|---|---|---|
| 208,227 A | 9/1878 | Dorr | |
| 972,983 A | 10/1910 | Arthur | |
| 1,003,232 A | 10/1910 | Cerbo | |
| 1,044,348 A | 6/1912 | Cerbo | |
| 1,328,624 A | 1/1920 | Graham | |
| 1,548,184 A | 8/1925 | Cameron | |
| 2,594,086 A | 4/1952 | Smith | |
| 2,704,064 A | 3/1955 | Fizzell et al. | |
| 2,736,002 A | 2/1956 | Oriel | |
| 2,808,826 A | 10/1957 | Reiner et al. | |
| 3,364,929 A | 1/1968 | Ide et al. | |
| 3,664,329 A | 5/1972 | Naylor | |
| 3,682,162 A | 8/1972 | Colyer | |
| 3,785,368 A | 1/1974 | McCarthy et al. | |
| 3,803,716 A | 4/1974 | Garnier | |
| 3,830,226 A | 8/1974 | Staub et al. | |
| 3,957,036 A | 5/1976 | Normann | |
| D245,789 S | 9/1977 | Shea et al. | |

(Continued)

FOREIGN PATENT DOCUMENTS

| | | |
|---|---|---|
| DE | 299 08 259 | 7/1999 |
| DE | 100 48 790 | 4/2002 |

(Continued)

OTHER PUBLICATIONS

Anatomy of the Lumbar Spine in MED TM MicroEndoscopic Discectomy (1997 Ludann Grand Rapids MI), 14 pgs.

(Continued)

*Primary Examiner* — Pedro Philogene
(74) *Attorney, Agent, or Firm* — Jonathan Spangler; Rory Schermerhorn

(57) ABSTRACT

Systems and methods are described for accessing and operating on an intervertebral disc at the lumbosacral junction via a trans-iliac approach. The instruments and methods described employ nerve monitoring to direct passage of the instruments through a safe zone between the L5 nerve root lying posterior to the trans-iliac path and the iliac vein (and iliac artery) lying anterior to the trans-iliac path.

20 Claims, 9 Drawing Sheets

(56) References Cited

U.S. PATENT DOCUMENTS

| | | |
|---|---|---|
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,226,288 A | 10/1980 | Collins, Jr. |
| 4,235,242 A | 11/1980 | Howson et al. |
| 4,285,347 A | 8/1981 | Hess |
| 4,291,705 A | 9/1981 | Severinghaus et al. |
| 4,449,532 A | 5/1984 | Storz |
| 4,461,300 A | 7/1984 | Christensen |
| 4,512,351 A | 4/1985 | Pohndorf |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,013 A | 6/1986 | Jones et al. |
| 4,595,018 A | 6/1986 | Rantala |
| 4,611,597 A | 9/1986 | Kraus |
| 4,616,635 A | 10/1986 | Caspar et al. |
| 4,633,889 A | 1/1987 | Talalla |
| 4,658,835 A | 4/1987 | Pohndorf |
| D295,445 S | 4/1988 | Freeman |
| 4,744,371 A | 5/1988 | Harris |
| 4,753,223 A | 6/1988 | Bremer |
| 4,759,377 A | 7/1988 | Dykstra |
| 4,784,150 A | 11/1988 | Voorhies et al. |
| 4,807,642 A | 2/1989 | Brown |
| D300,561 S | 4/1989 | Asa et al. |
| 4,892,105 A | 1/1990 | Prass |
| 4,913,134 A | 4/1990 | Luque |
| 4,917,274 A | 4/1990 | Asa et al. |
| 4,917,704 A | 4/1990 | Frey et al. |
| 4,926,865 A | 5/1990 | Oman |
| 4,950,257 A | 8/1990 | Hibbs et al. |
| 4,962,766 A | 10/1990 | Herzon |
| 4,964,411 A | 10/1990 | Johnson et al. |
| 5,007,902 A | 4/1991 | Witt |
| 5,015,247 A | 5/1991 | Michelson |
| 5,045,054 A | 9/1991 | Hood et al. |
| 5,052,373 A | 10/1991 | Michelson |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |
| 5,171,279 A | 12/1992 | Mathews |
| 5,192,327 A | 3/1993 | Brantigan |
| 5,195,541 A | 3/1993 | Obenchain |
| 5,196,015 A | 3/1993 | Neubardt |
| 5,215,100 A | 6/1993 | Spitz et al. |
| RE34,390 E | 9/1993 | Culver |
| D340,521 S | 10/1993 | Heinzelman et al. |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,295,994 A | 3/1994 | Bonutti |
| 5,299,563 A | 4/1994 | Seton |
| 5,312,417 A | 5/1994 | Wilk |
| 5,313,956 A | 5/1994 | Knutsson et al. |
| 5,313,962 A | 5/1994 | Obenchain |
| 5,327,902 A | 7/1994 | Lemmen |
| 5,331,975 A | 7/1994 | Bonutti |
| 5,333,618 A | 8/1994 | Lekhtman et al. |
| 5,342,384 A | 8/1994 | Sugarbaker |
| 5,357,983 A | 10/1994 | Mathews |
| 5,375,067 A | 12/1994 | Berchin |
| 5,375,594 A | 12/1994 | Cueva |
| 5,383,876 A | 1/1995 | Nardella |
| 5,395,317 A | 3/1995 | Kambin |
| 5,450,845 A | 9/1995 | Axelgaard |
| 5,472,426 A | 12/1995 | Bonati et al. |
| 5,474,057 A | 12/1995 | Makower et al. |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,487,739 A | 1/1996 | Aebischer et al. |
| 5,509,893 A | 4/1996 | Pracas |
| 5,514,153 A | 5/1996 | Bonutti |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,569,290 A | 10/1996 | McAfee |
| 5,571,149 A | 11/1996 | Liss et al. |
| 5,579,781 A | 12/1996 | Cooke |
| 5,593,429 A | 1/1997 | Ruff |
| 5,599,279 A | 2/1997 | Slotman et al. |
| 5,630,813 A | 5/1997 | Kieturakis |
| 5,667,508 A | 9/1997 | Errico et al. |
| 5,671,752 A | 9/1997 | Sinderby et al. |
| 5,681,265 A | 10/1997 | Maeda et al. |
| 5,688,223 A | 11/1997 | Rosendahl |
| 5,707,359 A | 1/1998 | Bufalini |
| 5,711,307 A | 1/1998 | Smits |
| 5,728,046 A | 3/1998 | Mayer et al. |
| 5,741,253 A | 4/1998 | Michelson |
| 5,741,261 A | 4/1998 | Moskovitz et al. |
| 5,759,159 A | 6/1998 | Masreliez |
| 5,762,629 A | 6/1998 | Kambin |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron |
| 5,792,044 A | 8/1998 | Foley et al. |
| 5,797,854 A | 8/1998 | Hedgecock |
| 5,797,909 A | 8/1998 | Michelson |
| 5,814,073 A | 9/1998 | Bonutti |
| 5,830,151 A | 11/1998 | Hadzic et al. |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,210 A | 3/1999 | Cox |
| 5,885,219 A | 3/1999 | Nightengale |
| 5,888,196 A | 3/1999 | Bonutti |
| 5,891,147 A | 4/1999 | Moskovitz et al. |
| 5,902,231 A | 5/1999 | Foley et al. |
| 5,928,139 A | 7/1999 | Koros et al. |
| 5,928,158 A | 7/1999 | Aristides |
| 5,931,777 A | 8/1999 | Sava |
| 5,935,131 A | 8/1999 | Bonutti et al. |
| 5,938,688 A | 8/1999 | Schiff |
| 5,944,658 A | 8/1999 | Koros et al. |
| 5,976,094 A | 11/1999 | Gozani et al. |
| 6,004,262 A | 12/1999 | Putz et al. |
| 6,004,312 A | 12/1999 | Finneran |
| 6,007,487 A | 12/1999 | Foley et al. |
| 6,010,520 A | 1/2000 | Pattison |
| 6,024,696 A | 2/2000 | Hoftman et al. |
| 6,024,697 A | 2/2000 | Pisarik |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,083,154 A | 7/2000 | Liu et al. |
| 6,095,987 A | 8/2000 | Shmulewitz |
| 6,104,957 A | 8/2000 | Alo et al. |
| 6,104,960 A | 8/2000 | Duysens et al. |
| 6,120,503 A | 9/2000 | Michelson |

(56) References Cited

U.S. PATENT DOCUMENTS

| | | |
|---|---|---|
| 6,126,660 A | 10/2000 | Dietz |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,146,335 A | 11/2000 | Gozani |
| 6,152,871 A | 11/2000 | Foley et al. |
| 6,159,179 A | 12/2000 | Simonson |
| 6,161,047 A | 12/2000 | King et al. |
| 6,174,311 B1 | 1/2001 | Branch et al. |
| 6,181,961 B1 | 1/2001 | Prass |
| 6,196,969 B1 | 3/2001 | Bester et al. |
| 6,206,826 B1 | 3/2001 | Mathews et al. |
| 6,217,509 B1 | 4/2001 | Foley et al. |
| 6,224,549 B1 | 5/2001 | Drongelen |
| 6,245,082 B1 | 6/2001 | Gellman et al. |
| 6,259,945 B1 | 7/2001 | Epstein et al. |
| 6,264,651 B1 | 7/2001 | Underwood et al. |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,308,712 B1 | 10/2001 | Shaw |
| 6,312,392 B1 | 11/2001 | Herzon |
| 6,325,764 B1 | 12/2001 | Griffith et al. |
| 6,334,068 B1 | 12/2001 | Hacker |
| 6,348,058 B1 | 2/2002 | Melkent et al. |
| 6,360,750 B1 | 3/2002 | Gerber et al. |
| 6,371,968 B1 | 4/2002 | Kogasaka et al. |
| 6,395,007 B1 | 5/2002 | Bhatnagar et al. |
| 6,425,859 B1 | 7/2002 | Foley et al. |
| 6,425,887 B1 | 7/2002 | McGuckin et al. |
| 6,425,901 B1 | 7/2002 | Zhu et al. |
| 6,450,952 B1 | 9/2002 | Rioux et al. |
| 6,451,015 B1 | 9/2002 | Rittman, III et al. |
| 6,466,817 B1 | 10/2002 | Kaula et al. |
| 6,468,205 B1 | 10/2002 | Mollenauer et al. |
| 6,468,207 B1 | 10/2002 | Fowler, Jr. |
| 6,500,116 B1 | 12/2002 | Knapp |
| 6,500,128 B2 | 12/2002 | Marino |
| 6,520,907 B1 | 2/2003 | Foley et al. |
| 6,524,320 B2 | 2/2003 | DiPoto |
| 6,535,759 B1 | 3/2003 | Epstein et al. |
| 6,564,078 B1 | 5/2003 | Marino et al. |
| 6,579,244 B2 | 6/2003 | Goodwin |
| 6,599,294 B2 | 7/2003 | Fuss et al. |
| 6,620,157 B1 | 9/2003 | Dabney et al. |
| 6,645,194 B2 | 11/2003 | Briscoe et al. |
| 6,679,833 B2 | 1/2004 | Smith et al. |
| 6,719,692 B2 | 4/2004 | Kleffner et al. |
| 6,760,616 B2 | 7/2004 | Hoey et al. |
| 6,770,074 B2 | 8/2004 | Michelson |
| 6,796,985 B2 | 9/2004 | Bolger et al. |
| 6,810,281 B2 | 10/2004 | Brock et al. |
| 6,819,956 B2 | 11/2004 | DiLorenzo |
| 6,829,508 B2 | 12/2004 | Schulman et al. |
| 6,847,849 B2 | 1/2005 | Mamo et al. |
| 6,849,047 B2 | 2/2005 | Goodwin |
| 6,855,105 B2 | 2/2005 | Jackson, III et al. |
| 6,869,398 B2 | 3/2005 | Obenchain |
| 6,871,099 B1 | 3/2005 | Whitehurst et al. |
| 6,902,569 B2 | 6/2005 | Parmer et al. |
| 6,916,330 B2 | 7/2005 | Simonson |
| 6,926,728 B2 | 8/2005 | Zucherman et al. |
| 6,929,606 B2 | 8/2005 | Ritland |
| 6,945,933 B2 | 9/2005 | Branch |
| 6,951,538 B2 | 10/2005 | Ritland |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,198,598 B2 | 4/2007 | Smith et al. |
| 7,207,949 B2 | 4/2007 | Miles et al. |
| 7,226,451 B2 | 6/2007 | Shluzas et al. |
| 7,261,688 B2 | 8/2007 | Smith et al. |
| 7,326,216 B2 * | 2/2008 | Bertagnoli et al. ............ 606/90 |
| 7,470,236 B1 | 12/2008 | Kelleher et al. |
| 7,473,222 B2 | 1/2009 | Dewey et al. |
| 7,481,766 B2 | 1/2009 | Lee et al. |
| 7,522,953 B2 | 4/2009 | Kaula et al. |
| 7,556,601 B2 | 7/2009 | Branch et al. |
| 7,582,058 B1 | 9/2009 | Miles et al. |
| 7,643,884 B2 | 1/2010 | Pond et al. |
| 7,691,057 B2 | 4/2010 | Miles et al. |
| 7,693,562 B2 | 4/2010 | Marino et al. |
| 7,717,959 B2 | 5/2010 | William et al. |
| 7,819,801 B2 | 10/2010 | Miles et al. |
| 7,935,051 B2 | 5/2011 | Miles et al. |
| 8,000,782 B2 | 8/2011 | Gharib et al. |
| 8,005,535 B2 | 8/2011 | Gharib et al. |
| 8,021,430 B2 | 9/2011 | Michelson |
| 8,133,173 B2 | 3/2012 | Miles et al. |
| 8,192,356 B2 * | 6/2012 | Miles et al. ............... 600/202 |
| 8,244,343 B2 * | 8/2012 | Gharib et al. ............... 600/546 |
| 8,245,570 B2 * | 8/2012 | Pickl et al. ............... 73/116.01 |
| 8,251,997 B2 | 8/2012 | Michelson |
| 8,303,458 B2 | 11/2012 | Fukano et al. |
| 8,343,046 B2 | 1/2013 | Miles et al. |
| 8,343,224 B2 | 1/2013 | Lynn et al. |
| 8,388,527 B2 | 3/2013 | Miles |
| 8,439,925 B2 | 5/2013 | Marino et al. |
| 2001/0039949 A1 | 11/2001 | Loubser |
| 2001/0056280 A1 | 12/2001 | Underwood et al. |
| 2002/0007129 A1 | 1/2002 | Marino |
| 2002/0010392 A1 | 1/2002 | Desai |
| 2002/0072686 A1 | 6/2002 | Hoey et al. |
| 2002/0077632 A1 | 6/2002 | Tsou |
| 2002/0123744 A1 | 9/2002 | Reynard |
| 2002/0123780 A1 | 9/2002 | Grill et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0070682 A1 | 4/2003 | Wilson et al. |
| 2003/0083688 A1 | 5/2003 | Simonson |
| 2003/0105503 A1 | 6/2003 | Marino |
| 2003/0139648 A1 | 7/2003 | Foley et al. |
| 2003/0149341 A1 | 8/2003 | Clifton |
| 2003/0225405 A1 | 12/2003 | Weiner |
| 2003/0236544 A1 | 12/2003 | Lunsford et al. |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0080320 A1 | 4/2005 | Lee et al. |
| 2005/0149035 A1 | 7/2005 | Pimenta et al. |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0198062 A1 | 8/2007 | Miles et al. |
| 2007/0293782 A1 | 12/2007 | Marino |
| 2008/0058606 A1 | 3/2008 | Miles et al. |
| 2008/0058838 A1 | 3/2008 | Steinberg |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0300465 A1 | 12/2008 | Feigenwinter et al. |
| 2009/0124860 A1 | 5/2009 | Miles et al. |
| 2009/0138050 A1 | 5/2009 | Ferree |
| 2009/0192403 A1 | 7/2009 | Gharib et al. |
| 2009/0204016 A1 | 8/2009 | Gharib et al. |
| 2010/0069783 A1 | 3/2010 | Miles et al. |
| 2010/0130827 A1 | 5/2010 | Pimenta et al. |
| 2010/0152603 A1 | 6/2010 | Miles et al. |
| 2010/0160738 A1 | 6/2010 | Miles et al. |
| 2010/0174146 A1 | 7/2010 | Miles |

(56) References Cited

U.S. PATENT DOCUMENTS

| | | | |
|---|---|---|---|
| 2010/0174148 | A1 | 7/2010 | Miles et al. |
| 2012/0010472 | A1* | 1/2012 | Spann .......................... 600/214 |
| 2012/0238822 | A1 | 9/2012 | Miles |

FOREIGN PATENT DOCUMENTS

| | | |
|---|---|---|
| EA | 0 972 538 | 1/2000 |
| EP | 0 334 116 | 9/1989 |
| EP | 1 002 500 | 5/2000 |
| FR | 2 795 624 | 1/2001 |
| JP | 793186 | 5/1990 |
| JP | 10-14928 | 3/1996 |
| KR | 3019990007098 | 11/1999 |
| WO | 0 567 424 | 10/1993 |
| WO | 94/28824 | 12/1994 |
| WO | 97/00702 | 1/1997 |
| WO | 98/23324 | 6/1998 |
| WO | 99/52446 | 10/1999 |
| WO | 00/27291 | 5/2000 |
| WO | 00/38574 | 7/2000 |
| WO | 00/44288 | 8/2000 |
| WO | 00/66217 | 11/2000 |
| WO | 00/67645 | 11/2000 |
| WO | 01/08563 | 2/2001 |
| WO | 01/37728 | 5/2001 |
| WO | 01/60263 | 8/2001 |
| WO | 02/054960 | 7/2002 |
| WO | 02/058780 | 8/2002 |
| WO | 02/71953 | 9/2002 |
| WO | 02/87678 | 11/2002 |
| WO | 03/005887 | 1/2003 |
| WO | 03/026482 | 4/2003 |
| WO | 03/037170 | 5/2003 |
| WO | 2005/013805 | 2/2005 |
| WO | 2005/030318 | 4/2005 |
| WO | 2006/042241 | 4/2006 |
| WO | 2006/066217 | 6/2006 |

OTHER PUBLICATIONS

Dirksmeier et al., "Microendoscopic and Open Laminotomy and Discectomy in Lumbar Disc Disease" *Seminars in Spine Surgery*, 1999, 11(2): 138-146.
METRx Delivered Order Form, 1999, 13 pages.
Medtronic Sofamor Danek "METRx™ MicroDiscectomy System," *Medtronic Sofamor Danek USA*,2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.
Japanese Patent Office JP Patent Application No. 2006-528306 Office Action with English Translation, Jun. 10, 2009, 4 pages.
Plaintiffs' Preliminary Invalidity Contentions re US Patents 7207949; 7470236 and 7582058, Sep. 18, 2009, 19 pages.
Plaintiffs' Preliminary Invalidity Contentions—Appendices, Sep. 18, 2009, 191 pages.
Plaintiffs' Supplemental Preliminary Invalidity Contentions re US Patents 7207949, 7470236, and 7582058, Sep. 29, 2009, 21 pages.
Plaintiffs' Supplemental Preliminary Invalidity Contentions-Appendices, Sep. 29, 2009, 294 pages.
Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.

Medtronic Sofamor Danek "UNION™ / UNION-L™ Anterior & Lateral Impacted Fusion Devices: Clear choice of stabilization," *Medtronic Sofamor Danek*, 2000, 4 pages.
NuVasive Vector™Cannulae, 2000, 1 page.
NuVasive Triad™Tri-Columnar Spinal EndoArthrodesis™via Minimally Invasive Guidance, 2000, 1 page (prior to Sep. 25, 2003).
NuVasive Triad™Cortical Bone Allograft, 2000, 1 page (prior to Sep. 25, 2003).
NuVasive Vertebral Body Access System, 2000, 1 page.
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasive™Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25 2003).
Isley et al., "Recent Advances in Intraoperative Neuromonitoring of Spinal Cord Function: Pedicle Screw Stimulation Techniques," *American Journal of Electroneurodiagnostic Technology*, Jun. 1997, 37(2): 93-126.
Mathews et al., "Laparoscopic Discectomy with Anterior Lumbar Interbody 20(16): 1797-1802 Fusion," *SPINE*, 1995,20(16): 1797-1802.
Rose et al., "Persistently Electrified Pedicle Stimulation Instruments in Spinal Instrumentation: Techniques and Protocol Development," *SPINE*, 1997, 22(3): 334-343.
"Electromyography System," International Search report from International Application No. PCT/US00/32329, Apr. 27, 2001, 9 pages.
"Nerve Proximity and Status Detection System and Method," International Search Report from International Application No. PCT/US01/18606, Oct. 18, 2001, 6 pages.
"Relative Nerve Movement and Status Detection System and Method," International Search Report from International Application No. PCT/US01/18579, Jan. 15, 2002, 6 pages.
"System and Method for Determining Nerve Proximity Direction and Pathology During Surgery," International Search Report from International Application No. PCT/US02/22247, Mar. 27, 2003, 4 pages.
"System and Methods for Determining Nerve Direction to a Surgical Instrument," International Search Report from International Application No. PCT/US03/02056, Aug. 12, 2003, 5 pages.
"Systems and Methods for Performing Percutaneous Pedicle Integrity Assessments," International Search Report from International Application No. PCT/US02/35047, Aug. 11, 2003, 5 pages.

(56) References Cited

OTHER PUBLICATIONS

"Systems and Methods for Performing Surgery Procedures and Assessments," International Search Report from International Application No. PCT/US02/30617, Jun. 5, 2003, 4 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with stimulus-evoked EMG," *Spine*, Department high electrical resistance: a potential source of error with of Orthopaedic Surgery University of Virginia, Jul. 15, 2002, 27(14): 1577-1581.
Bose et al., "Neurophysiologic Monitoring of Spinal Nerve Root Function During Instrumented Posterior Lumber Spine Surgery," *Spine*, 2002, 27(13):1444-1450.
Calancie et al., "Stimulus-Evoked EMG Monitoring During Transpedicular Lumbosacral Spine Instrumentation" *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," *Spine*, Charlotte Spine Center North Carolina, Jan., 15, 1998, 23(2): 256-262.
Ebraheim et al., "Anatomic Relations Between the Lumbar Pedicle and the Adjacent Neural Surgery Structures," *Spine*, Department of Orthopaedic Medical College of Ohio, Oct. 15, 1997, 22(20): 2338-2341.
Ford et al. "Electrical Characteristics of Peripheral Nerve Stimulators Implications for Nerve Localization," *Regional Anesthesia*, 1984, 9: 73-77.
Glassman et al., "A Prospective Analysis of Intraoperative Electromyographic Monitoring of Pedicle Screw Placement With Computed Tomographic Scan Confirmation," *Spine*, 1995, 20(12): 1375-1379.
Greenblatt et al., "Needle Nerve Stimulator-Locator: Nerve Blocks with a New Instrument for Locating Nerves," *Anesthesia & Analgesia*, 1962, 41(5): 599-602.
Haig, "Point of view," *Spine*, 2002, 27(24): 2819.
Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.
Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.
Holland, "Intraoperative Electromyography During Thoracolumbar Spinal Surgery," *Spine*, 1998, 23(17): 1915-1922
Journee et al., "System for Intra-Operative Monitoring of the Cortical Integrity of the Pedicle During Pedicle Screw Placement in Low-Back Surgery: Design and Clinical Results", *Sensory and Neuromuscular Diagnostic Instrumentation and Data Analysis I, 18th Annual International Conference on Engineering in Medicine and Biology Society*, Amsterdam, 1996, pp. 144-145.
Maguire et al., "Evaluation of Intrapedicular Screw Position Using Intraoperative Evoked Electromyography," *Spine*, 1995, 20(9): 1068-1074.

Martin et al. "Initiation of Erection and Semen Release by Rectal Probe Electrostimulation (RPE)," *The Journal of Urology*, The Williams & Wilkins Co., 1983, 129: 637-642.
Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.
Pither et al., "The Use of Peripheral Nerve Stimulators for Regional Anesthesia: Review of Experimental Characteristics Technique and Clinical Applications," *Regional Anesthesia*, 1985, 10:49-58
Raj et al., "Infraclavicular Brachial Plexus Block—A New Approach" *Anesthesia and Analgesia*, 1973, (52)6: 897-904.
Raj et al., "The Use of Peripheral Nerve Stimulators for Regional Anesthesia," *Clinical Issues in Regional Anesthesia*, 1985, 1(4):1-6
Raj et al., "Use of the Nerve Stimulator for Peripheral Blocks," *Regional Anesthesia*, Apr.-Jun. 1980, pp. 14-21.
Raymond et al., "The Nerve Seeker: A System for Automated Nerve Localization," *Regional Anesthesia*, 1992, 17(3): 151-162.
Shafik, "Cavernous Nerve Simulation through an Extrapelvic Subpubic Approach: Role in Penile Erection," *Eur. Urol*, 1994, 26: 98-102.
Toleikis et al., "The Usefulness of Electrical Stimulation for Assessing Pedicle Screw Replacements," *Journal of Spinal Disorder*, 2000, 13(4): 283-289.
Medtronic Sofamor Danek "UNION™/UNION-L™ Anterior & Lateral Impacted Fusion Devices: Surgical Technique" *Medtronic Sofamor Danek*, 2001, 20 pages.
Defendant's Disclosure of Asserted Claims and Preliminary Infringement Contentions Regarding USP 7207949; 7470236 and 7582058, Aug. 31, 2009, 21 pages.
Bergey et al., "Endoscopic Lateral Transpsoas Approach to the Lumbar Spine," *Spine*, 2004, 29(15):1681-1688.
Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.
Gardocki, "Tubular diskectomy minimizes collateral damage: A logical progression moves spine surgery forward," *AAOS Now*, 2009, 5 pages.
Hovorka et al., "Five years' experience of retroperitoneal lumbar and thoracolumbar surgery," *Eur. Spine J.*, 2000, 9(1): S30-S34.
Kossmann et al., "The use of a retractor system (SynFrame) for open, minimal invasive reconstruction of the anterior column of the thoracic and lumbar spine," *Eur Spine J.*, 2001, 10:396-402.
Mayer, "A New Microsurgical Technique for Minimally Invasive Anterior Lumbar Interbody Fusion," *Spine*, 1997, 22(6): 691-699.
Mayer, "The ALIF Concept," *Eur Spine J.*, 2000, 9(1):S35-S43.
Mayer and Wiechert, "Microsurgical Anterior Approaches to the Lumbar Spine for Interbody Fusion and Total Disc Replacement," *Neurosurgery*, 2002, 51(2): 159-165.
McAfee et al., "Minimally Invasive Anterior Retroperitoneal Approach to the Lumbar Spine: Emphasis on the Lateral BAK," *Spine*, 1998, 23(13): 1476-1484.
Rao, et al. "Dynamic retraction of the psoas muscle to expose the lumbar spine using the retroperitoneal approach," *J. Neurosurg Spine*, 2006, 5: 468-470.
Wolfla et al., "Retroperitoneal lateral lumbar interbody fusion with titanium threaded fusion cages," *J. Neurosurg (Spine 1)*, 2002, 96: 50-55.
Larson and Maiman, "Surgery of the Lumbar Spine," Thieme Medical Publishers, Inc., 1999, pp. 305-319.
Medtronic XOMED Surgical Products, Inc., NIM-Response Nerve Integrity Monitor Intraoperative EMG Monitor User's Guide, Revision B, 2000, 47 pages.
"NuVasive's spine surgery system cleared in the US," Pharm & Medical Industry Week, Dec. 10, 2001, 1 page.
Pimenta, "Initial Clinical Results of Direct Lateral, Minimally Invasive Access to the Lumbar Spine for Disc Nucleus Replacement Using a Novel Neurophysiological Monitoring System." *The 9th IMAST*, May, 2002, 1 page.
Pimenta et al., "The Lateral Endoscopic Transpsoas Retroperitoneal Approach (Letra) for Implants in the Lumbar Spine," *World Spine II—Second Interdisciplinary Congress on Spine Care*, Aug. 2003, 2 pages.

(56) References Cited

OTHER PUBLICATIONS

Crock, H.V. MD., "Anterior Lumbar Interbody Fusion," Clinical Orthopaedics and Related Research, Number One Hundred Sixty Five, 1982, pp. 157-163, 13 pages.

Mayer and Brock, "Percutaneous endoscopic discectomy: surgical technique and preliminary results compared to microsurgical discectomy," *J. Neurosurg*, 1993, 78: 216-225.

Schaffer and Kambin, "Percutaneous Posterolateral Lumbar Discectomy and Decompression with a 6.9-Millimeter Cannula," *The Journal of Bone and Joint Surgery*, 1991, 73A(6): 822-831.

Friedman, "Percutaneous discectomy: An alternative to chemonucleolysis," *Neurosurgery*, 1983, 13(5): 542-547.

Request for *Inter Partes*Reexamination in re U.S. Patent 7,905,840, dated Feb. 8, 2012, 204 pages.

Brau, "Chapter 22: Anterior Retroperitoneal Muscle-Sparing approach to L2-S1 of the Lumbar Spine," *Surgical Approaches to the Spine*. Robert G. Watkins, MD. (ed) 2003. Pages 165-181.

Kossmann et al., "Minimally Invasive Vertebral Replacement with Cages in Thoracic and Lumbar Spine," *European Journal of Trauma*, 2001, 27: 292-300.

Mayer H. M. (ed.) *Minimally Invasive Spine Surgery: A Surgical Manual*. 2000. 51 pages.

Pimenta et al., "Implante de protese de nucleo pulposo: analise inicial," *Journal Brasileiro de Neurocirurgia*, 2001, 12(2): 93-96.

Traynelis, "Spinal Arthroplasty," *Neurological Focus*, 2002, 13(2): 12 pages.

Zdeblick, Thomas A. (ed.). Anterior Approaches to the Spine. 1999. 43 pages.

Amended Complaint for *NuVasive, Inc.* v. *Globus Medical, Inc.*, Case No. 1:10-cv-0849 (D. Del., Oct. 5, 2010), 28 pages.

Request for *Inter Partes*Reexamination in re U.S. Patent 7,819,801, dated Feb. 8, 2012, 89 pages.

Kossman et al., "The use of a retractor system (SynFrame) for open, minimal invasive reconstruction of the anterior column of the thoracic and lumbar spine," *Eur Spine J*, 2001, 10: 396-402.

de Peretti et al., "New possibilities in L2-L5 lumbar arthrodesis using a lateral retroperitoneal approach assisted by laparoscopy: preliminary results," *Eur Spine J*, 1996, 5: 210-216.

Litwin et al., "Hand-assisted laparoscopic surgery (HALS) with the handport system," *Annals of surgery*, 2000, 231(5): 715-723.

Acland's Video Atlas of Human Anatomy, Section 3.1.7: Paravertebral Muscles. Available online: http://aclandanatomy.com/abstract/4010463. Accessed Jul. 11, 2012.

MedlinePlus, a Service of the U.S. National Library of Medicine and National Institutes of Health. Available online: http://www.nlm.nih.gov/medlineplus/. Accessed Jul. 11, 2012.

Baulot et al., Adjuvant Anterior Spinal Fusion Via Thoracoscopy, *Lyon Chirurgical*, 1994, 90(5): 347-351 including English Translation And Certificate of Translation.

Leu et al., "Percutaneous Fusion of the Lumbar Spine," *Spine*, 1992, 6(3): 593-604.

Rosenthal et al., "Removal of a Protruded Thoracic Disc Using Microsurgical Endoscopy," *Spine*, 1994, 19(9): 1087-1091.

Counterclaim Defendants' Corrected Amended Invalidity Contentions re U.S. Patent Nos. 8,000,782; 8,005,535; 8,016,767; 8,192,356; 8,187,334; 8,361,156, D652,922; D666,294 re Case No. 3:12-cv-02738-CAB(MDD), dated Aug. 19, 2013, 30 pages.

Petition for Inter Partes Review IPR2014-00034, filed Oct. 8, 2013, 65 pages.

Petition for Inter Partes Review IPR2014-00035, filed Oct. 8, 2013, 65 pages.

Declaration of Lee Grant, from IPR2014-00034, Oct. 7, 2013, 36 pages.

Declaration of David Hacker from IPR2014-00034, Oct. 4, 2013, 64 pages.

NuVasive, Inc's Opening Claim Construction Brief Regarding U.S. Patent Nos. 8,000,782; 8,005 535; 8,016,767; 8,192,356; 8,187,334; 8,361,156, D652,922; and 5,676,146 C2, filed Sep. 3, 2013, in *Warsaw Orthopedic, Inc.* v. *NuVasive, Inc.*, No. 3:12-cv-02738-CAB-MDD (S.D. Cal.)., 34 pages.

Petition for Inter Partes Review IPR2014-00073, filed Oct. 18, 2013, 65 pages.

Petition for Inter Partes Review IPR2014-00074, filed Oct. 18, 2013, 65 pages.

Petition for Inter Partes Review IPR2014-00075, filed Oct. 21, 2013, 66 pages.

Petition for Inter Partes Review IPR2014-00076, filed Oct. 21, 2013, 65 pages.

Petition for Inter Partes Review IPR2014-00081, filed Oct. 22, 2013, 64 pages.

Petition for Inter Partes Review IPR2014-00087, filed Oct. 22, 2013, 64 pages.

Declaration of Lee Grant, from IPR2014-00073, Oct. 9, 2013, 36 pages.

Declaration of David Hacker, from IPR2014-00073, Oct. 10, 2013, 64 pages.

U.S. Appl. No. 60/392,214, filed Jun. 26, 2002, 97 pages.

Amendment in reply to Feb. 15, 2012 Office Action in U.S. Appl. No. 12/635,418, dated Mar. 16, 2012, 24 pages.

Decision on Appeal in *Inter Partes* Reexamination U.S. Appl. No. 95/001,247, dated Mar. 18, 2013, 49 pages.

Declaration of Lee Grant, from IPR2014-00074, Oct. 9, 2013, 36 pages.

Declaration of David Hacker, from IPR2014-00074, Oct. 10, 2013, 64 pages.

Declaration of David Hacker, from IPR2014-00075, Oct. 10, 2013, 64 pages.

Amendment in reply to Action of Feb. 7, 2011 and Notice of May 12, 2011, in U.S. Appl. No. 11/789,284, dated May 17, 2011, 16 pages.

Notice of Allowance in U.S. Appl. No. 11/789,284, dated Jul. 18, 2011, 8 pages.

Office action from U.S. Appl. No. 11/789,284, dated Feb. 7, 2011, 10 pages.

Merriam-Webster's Collegiate Dictionary, p. 65 (10th ed. 1998).

Declaration of Lee Grant, from IPR2014-00076, Oct. 9, 2013, 36 pages.

Moed et al., "Evaluation of Intraoperative Nerve-Monitoring During Insertion of an Iliosacral Implant in an Animal Model, *Journal of Bone and Joint Surgery*," 1999, 81-A(11): 9.

Declaration of Lee Grant, from IPR2014-0081, Oct. 9, 2013, 36 pages.

Declaration of David Hacker from IPR2014-00081, Oct. 10, 2013, 64 pages.

U.S. Appl. No. 60/325,424, filed Sep. 25, 2001, 346 pages.

Declaration of Lee Grant, from IPR2014-0087, Oct. 9, 2013, 36 pages.

Declaration of David Hacker from IPR2014-00087, Oct. 10, 2013, 64 pages.

Request for *Inter Partes* Reexamination in re: U.S. Patent 7,691,057, dated Feb. 8, 2012, 50 pages.

Declaration of Daniel Schwartz, Ph.D. from IPR2014-00034, Oct. 7, 2013, 1056 pages.

Declaration of Daniel Schwartz, Ph.D. from IPR2014-00035, Oct. 7, 2013, 661 pages.

510(K) No. K002677, approved by the FDA on Nov. 13, 2000, 634 pages.

510(K) No. K013215, approved by the FDA on Oct. 16, 2001, 376 pages.

Declaration of Robert G. Watkins, from IPR2014-00073, Oct. 18, 2013, 1101 pages.

Declaration of Daniel Schwartz, from IPR2014-00073, Oct. 12, 2013, 1226 pages.

Declaration of Robert G. Watkins, from IPR2014-00074, Oct. 18, 2013, 548 pages.

Declaration of Daniel Schwartz, from IPR2014-00074, Oct. 12, 2013, 565 pages.

Declaration of Robert G. Watkins, from IPR2014-00075, Oct. 18, 2013, 674 pages.

Declaration of Daniel Schwartz, from IPR2014-00075, Oct. 12, 2013, 1107 pages.

(56) References Cited

OTHER PUBLICATIONS

Declaration of Robert G. Watkins, from IPR2014-00076, Oct. 18, 2013, 543 pages.
Declaration of Daniel Schwartz, from IPR2014-00076, Oct. 12, 2013, 1247 pages.
Declaration of David Hacker, from IPR2014-00076, Oct. 10, 2013, 64 pages.
Declaration of Daniel Schwartz, from IPR2014-0081, Oct. 21, 2013, 585 pages.
Declaration of Daniel Schwartz from IPR2014-0087, Oct. 21, 2013, 585 pages.

* cited by examiner

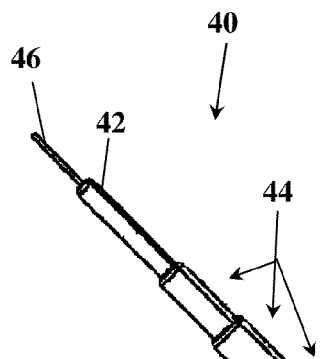
FIG. 8
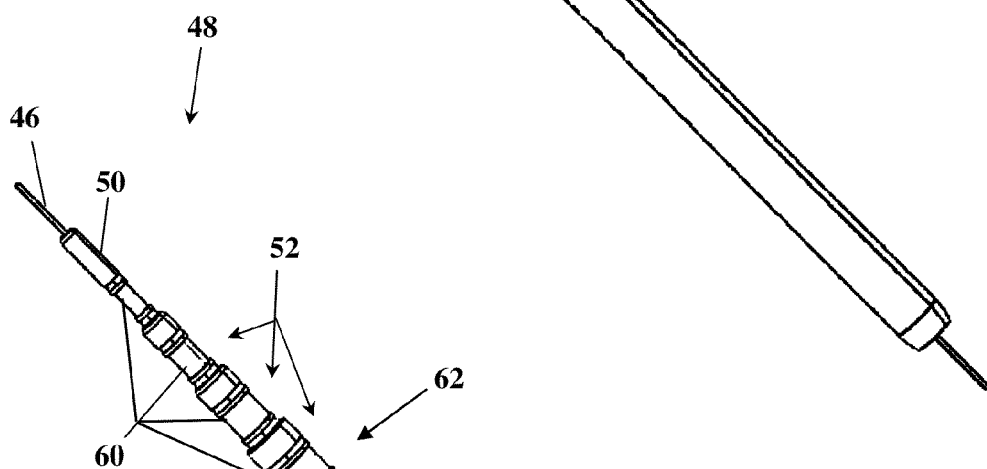
FIG. 9
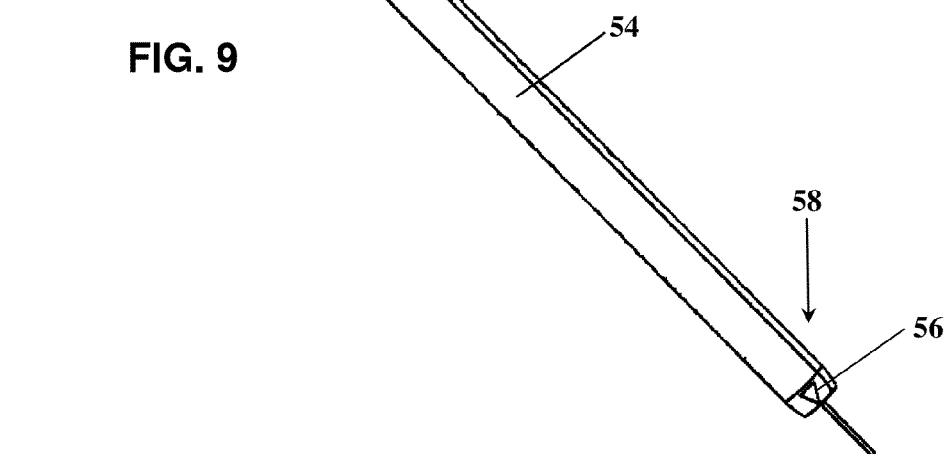

SYSTEMS AND METHODS FOR PERFORMING SPINE SURGERY

CROSS-REFERENCE TO RELATED APPLICATIONS

This application is an non-provisional patent application and claims the benefit of priority from U.S. Provisional Patent Application Ser. No. 61/471,069, entitled "Systems and Methods for Performing Spine Surgery," filed on Apr. 1, 2011, the entire contents of which is expressly incorporated by reference into this disclosure as if set forth in its entirety herein.

FIELD

The present invention relates to implants and methods for accessing and operating on the lumbosacral spine.

BACKGROUND

The spinal column is a highly complex system of bones and connective tissues that provide support for the body and protect the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease or trauma, such as ruptured or slipped discs, degenerative disc disease, fractured vertebra and the like. Patients that suffer from such conditions usually experience extreme and debilitating pain, as well as diminished nerve function.

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. On such minimally invasive approach, a lateral trans-psoas approach to the spine, developed by NuVasive®, Inc., San Diego, Calif. (XLIF®) has demonstrated great success in reducing patient morbidity, shortening hospitalization stays and quickening recovery time if it is employed.

Unfortunately, the iliac crest blocks lateral access to the L5/S1 disc space in most individuals, leaving only anterior and posterior approaches available to reach the L5/S1 disc. Thus, in a patient requiring a multi-level operation including L5-S1, for example, a lateral trans-psoas approach may be utilized to treat the spinal condition at one or more levels above the L5/S1 disc, and the patient may be moved into a new position to access the L5/S1 disc through either the anterior or posterior approach. The systems and methods described herein are directed towards eliminating, or at least reducing, these challenges.

The present invention is directed at overcoming, or at least improving upon, the disadvantages of the prior art.

SUMMARY

Access to the L5/S1 disc space (also referred to as the 5-1 disc) may be achieved laterally through the iliac crest. One or more instruments are used to create an access hole through the iliac over the L5/S1 disc. Through the access hole one or more instruments may be advanced to the L5/S1 disc, taking care to avoid damaging delicate nerves and blood vessels situated in the space between the iliac crest and spinal column. One of the one or more instruments advanced to the disc space may be a working portal through which the disc may be operated on (e.g. discectomy and fusion may be performed).

FIGS. 3-5 illustrate the iliac crest, L5/S1 disc, and the space that separates them—referred to herein as the iliac space. As best appreciated in FIGS. 3-4 traversing the path between the iliac crest and the L5/S1 disc is complicated by an abundance of nerve tissue and vascular tissue. Of particular concern are the L5 nerve root and the iliac vein and iliac artery as damage to any of these tissues could result in serious consequences to the patient. However, as best pictured in FIGS. 6-8, it is possible to access the 5-1 disc through the space between the L5 nerve root and the iliac vein. This space is termed the "safe zone" herein and is bordered posteriorly by the L5 nerve root and anteriorly by the iliac vein. Transiliac access to the 5-1 disc may thus be safely achieved by passing an access device through the safe zone to the disc to create a corridor through which work on the disc may be performed without danger to the vessels or nerve root.

The precise size and location of the safe zone may vary from patient to patient, thus it is important to assess the safe zone prior to creating the access corridor. The safe zone may be assessed through pre-operatively through the study of pre-operative images (e.g. CT scans and/or MRI). The L5 nerve root and the iliac vein (and artery) can be identified in the images and the size of the safe zone determined. By way of example, the size of the safe zone may generally vary between a range of approximately 10 mm and 20 mm, though the range is not inclusive.

Once the safe zone has been assessed during pre-operative planning, the information may be used during surgery to avoid the iliac vessels and the L5 nerve root. This is accomplished by using nerve monitoring techniques to locate the L5 nerve root. By way of example, stimulation signals are emitted from the distal end of an access instrument (e.g. dilator) and muscles innervated by the nerve are monitored for a neuromuscular response. The stimulation current level required to elicit a significant response (stimulation threshold) is determined, and preferably repeatedly updated, which provides an indication of the nerve proximity (and optionally, direction) to the distal end of the access instrument. The higher the stimulation threshold the farther away the nerve is, and vice versa. Thus, to seek out the L5 nerve root the user can direct the access instrument such that the stimulation threshold gets lower and lower (indicating that the access instrument is getting closer to the nerve) until the threshold drops below a certain level (e.g. 3 mA) indicating that the instrument is right next to the nerve, but not contacting the nerve. Directionality may be determined to ensure that the instrument is anterior to the nerve. With the position of the nerve now know, the position of the iliac vein is also known (based on the pre-operative planning data) and the access instrument may be docked to the 5-1 disc in the safe zone. By following the path of the initial access instrument, additional instruments can safely advance through to the L5/S1 disc and the desired procedure may be completed on the disc. Nerve monitoring may be conducted with one or more of the additional instruments.

As described herein, two sets of dilators are used to create the access corridor to the 5-1 disc. The first set of dilators is used for dilating the iliac crest and the dilators are designed to be impacted through the iliac bone. The second set of dilators are used for dilating through the iliac space and are designed to be used with a neurophysiology monitoring system to determine the location of the L5 nerve root as the dilators are advanced. It should be appreciated that two different sets of dilators are not necessarily required, provided that the both functions (i.e. impaction through bone and nerve monitoring) may be completed with the dilators chosen.

According to the example method described, a jamshidi is first advanced into the iliac bone at the appropriate entry point. The needle of the jamshidi is removed and a K-wire or similar guide is advanced into the iliac. The cannula of the jamshidi is removed and the initial dilator of the first dilator set (impaction dilators) is advanced into the iliac crest, over the K-wire, and wagged around. The supplemental dilators of the first dilator set are the advanced in turn into the iliac bone until the access hole created is of the appropriate size. The dilators are then removed and the initial dilator of the second dilator set (electrified dilators) is advanced to the access hole. The initial dilator is connected to the neurophysiology monitoring system to perform nerve detection as described above and the dilator is advanced toward the L5 nerve root. Once the nerve root is located the initial dilator is docked in the desired position on the 5-1 disc with the K-wire. The supplemental dilators of the second set of dilators are then advanced in turn through the safe zone onto the disc space until the desired size is achieved. The outer dilator is fixed in position (e.g. by penetrating into the disc or vertebral body, or, with a table mount) and the inner dilators are removed.

The inner lumen of the outer dilator becomes a working portal through which instruments may be passed to perform the desired procedure on the L5/S1 disc. For example, the instruments may be curettes, reamers, shavers, etc. . . . for performing a discectomy. Implants may also be deposited in the disc space to facilitate fusion. The implant may be a collapsible bag that is advanced through the working corridor in a collapsed configuration and then filled with a filler material in situ. The filler material may be a bone growth promoting material (e.g. bone chips, synthetic or cellular bone matrix, etc. . . . ). The implant may also be an expandable implant that is implanted into the disc space in a first smaller configuration and then expanded via any number of suitable expansion mechanisms. The implant may also be a modular implant that is inserted through the working portal in several smaller pieces and assembled in the disc space to form a larger implant. Bone growth promoting material may be packed in or around any of the implants described. Once work on the 5-1 disc is complete, the working portal is removed and the wound closed.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 6 is a top down view of the S1 vertebra depicting relative to the L5/S1 disc the position of the L5 nerve root, the iliac vessels, and the safe zone situated there between;

FIG. 8 is a perspective view of a first (impaction) dilator set that may be used during formation of a trans-iliac access corridor to the L5/S1 disc, according to one example embodiment;

FIG. 9 is a perspective view of a second (nerve monitoring) dilator set that may be used during formation of a trans-iliac access corridor to the L5/S1 disc, according to one example embodiment.

DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The methods and devices described herein include a variety of inventive features and components that warrant patent protection, both individually and in combination.

As described hereafter, access to the L5/S1 disc space is achieved laterally through the ilium. One or more instruments are used to create an access hole through the ilium over top of the L5/S1 disc. Through the access hole one or more instruments may be advanced to the L5/S1 disc, taking care to avoid damaging delicate nerves and blood vessels situated in the space between the iliac crest and spinal column. One of the one or more instruments advanced to the disc space may form a working portal through which the disc may be operated on, for example, a discectomy and fusion may be performed.

Figure 1:
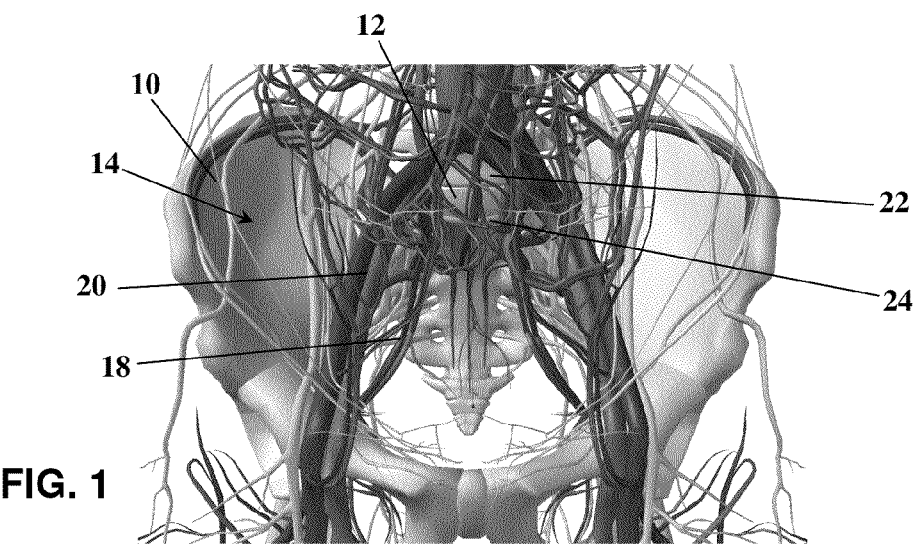
FIG. 1 is an anterior view of the skeletal, nerve, and blood vessel anatomy in and around the iliac space.
Figure 2:
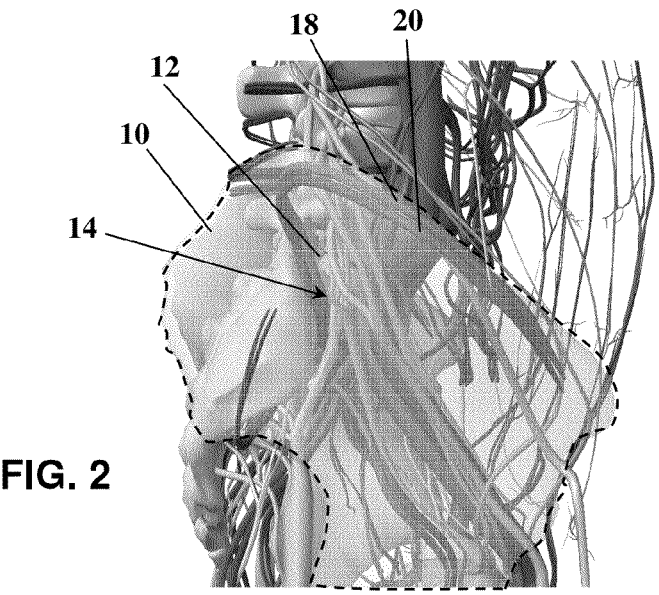
FIG. 2 is a lateral view looking through the ilium of the skeletal, nerve, and blood vessel anatomy in and around the iliac space.
Figure 3:
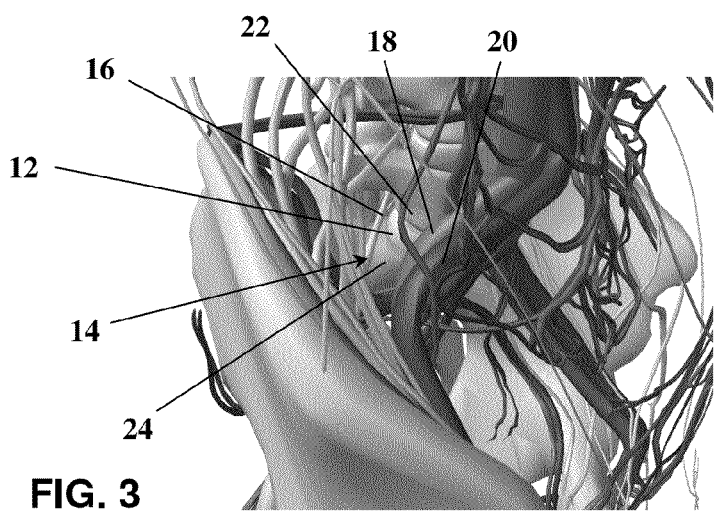
FIG. 3 is a lateral perspective is a perspective view of a first (impaction) dilator set that may be used during formation of a trans-iliac access corridor to the L5/S1 disc, according to one example embodiment.
Figure 4:
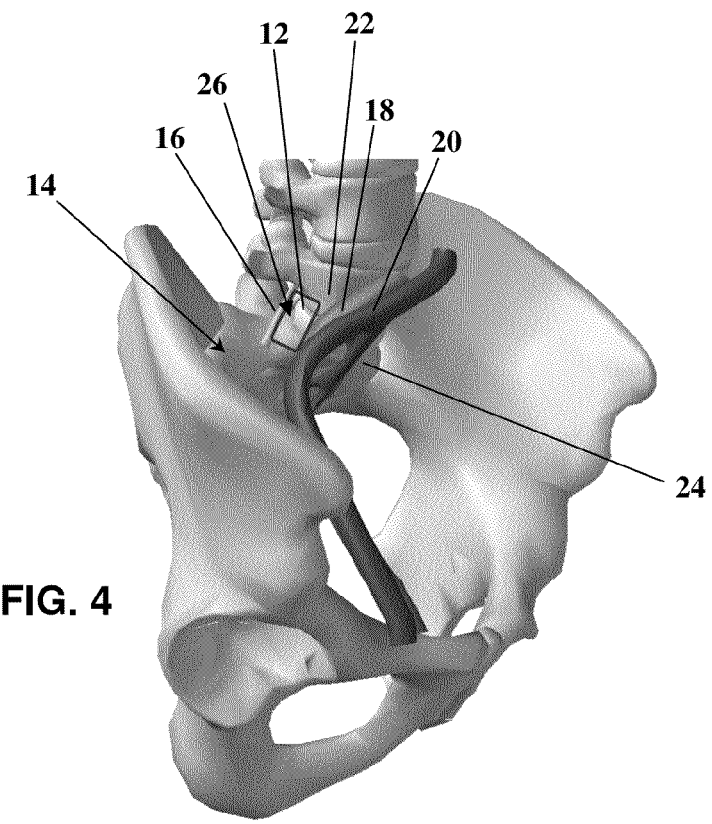
FIG. 4 is the lateral perspective view of FIG. 3 with all but the L5 nerve root and iliac vessels hidden and highlighting a safe zone between the L5 nerve root and iliac vessels through which an access corridor to the L5/S1 disc may be created, according to one example embodiment.
Figure 5:
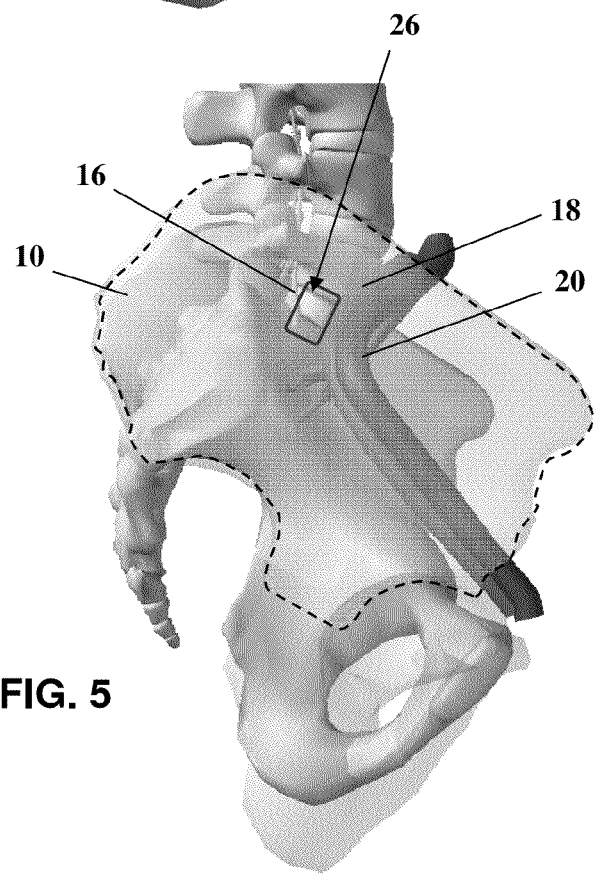
FIG. 5 is a lateral view looking through the ilium with all but the L5 nerve root and iliac vessels hidden and highlighting a safe zone between the L5 nerve root and iliac vessels through which an access corridor to the L5/S1 disc may be created, according to one example embodiment.
Figure 6:
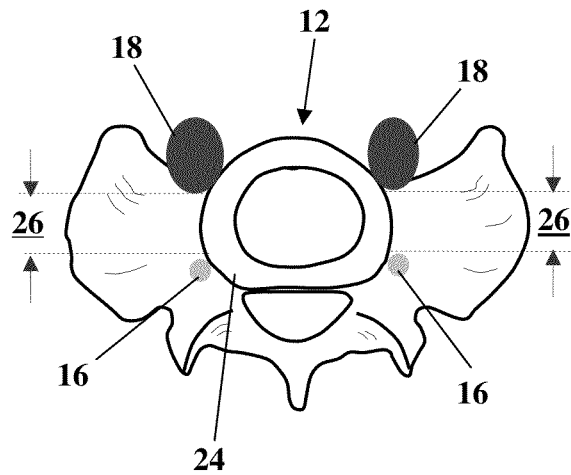

Prior to describing the trans-iliac method for access the L5/S1 disc, the relevant anatomy, including the iliac crest 10, L5/S1 disc 12, and the space that separates them—referred to herein as the iliac space 14, are described with reference to FIGS. 1-6. As best appreciated in FIGS. 1-3, the iliac space 14 between the iliac crest 10 and the L5/S1 disc 12 is filled with an abundance of nerve and vascular tissue. Of particular concern when traversing the iliac space 14 are the L5 nerve root 16, the iliac vein 18, and iliac artery 20, as damage to any of these delicate tissues could result in serious consequences to the patient. FIGS. 4-5 highlight the position of these structures (L5 nerve root 16, iliac vein 18, and iliac artery 20) with the remaining peripheral tissues hidden for the sake of clarity. There is a small space between the L5 nerve root 16, which exits the spinal canal just posterior to the L5 vertebral body 22 and S1 vertebral body 24, and the iliac vein 18, which passes along an anterior portion of the lateral side of the L5 and S1 vertebral bodies 22, 24. This small space represents a window through which the L5/S1 disc may be access. This window is termed the "safe zone" 26 herein and is bordered posteriorly by the L5 nerve root 16 and anteriorly by the iliac vein 18. Thus, trans-iliac access to the L5/S1 disc 12 may be safely achieved by passing an access device through the safe zone 14 to the disc 12 to create a corridor through which work on the disc may be performed without danger to the vessels or nerve root.

The size and precise layout of the safe zone 26 varies from patient to patient. For example, though not limited to it, the size of the safe zone (i.e. distance between the L5 nerve root 16 and iliac vein 18) may generally range from approximately 10 mm to 20 mm. Accordingly, it is preferable that the safe zone be identified and assessed during pre-operative planning. This is accomplished through the review of CT and/or MRI images on which the L5 nerve root 16 and the iliac vein 18 can be identified and the distance between them measured. This information will then be used later during the procedure to ensure the access instrument(s) stay within the safe zone during passage through the iliac space 14.

Figure 7:
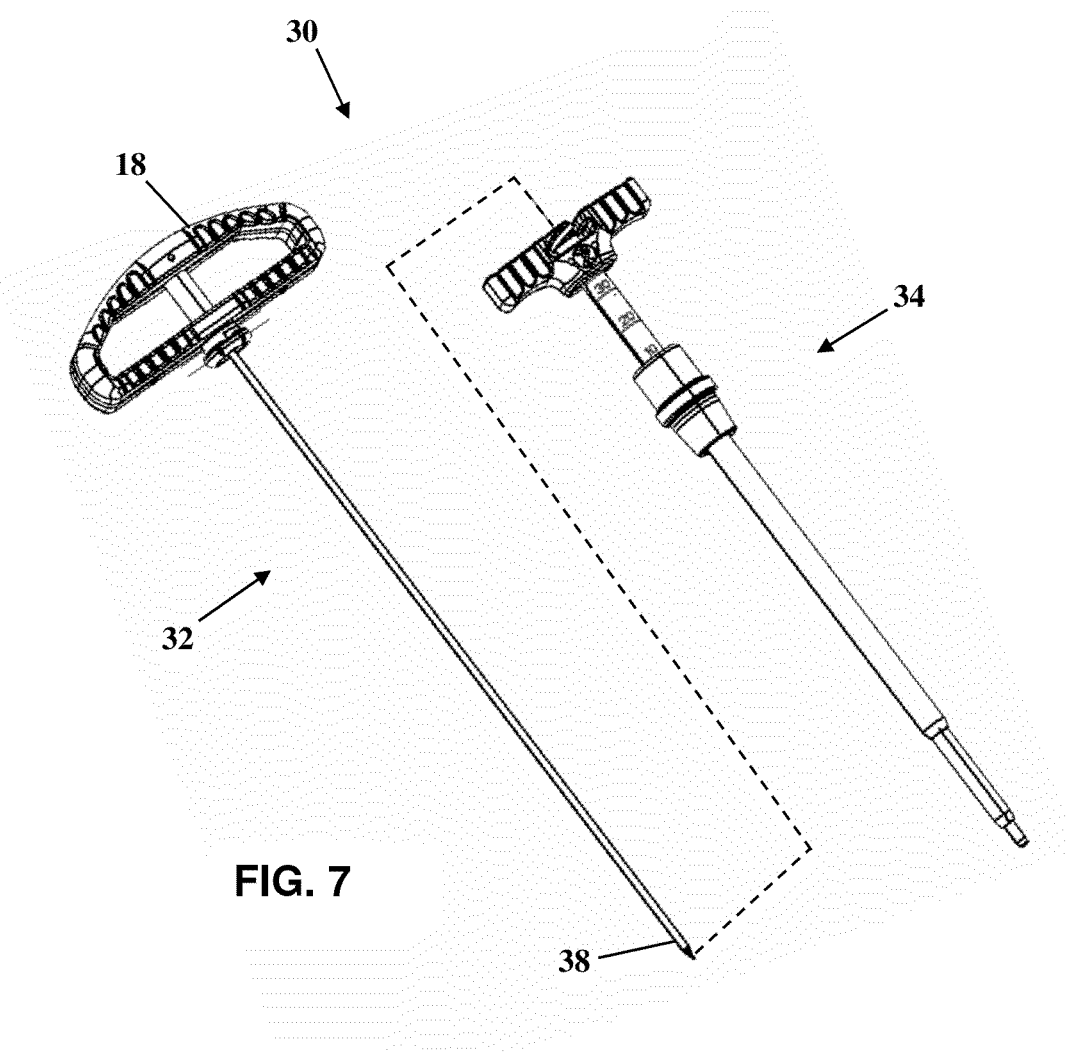
FIG. 7 is a perspective view of a jamshidi like needle that may be used during formation of a trans-iliac access corridor to the L5/S1 disc, according to one example embodiment.

According to the example method described herein, L5/S1 access is achieved using a jamshidi type needle, K-wire, and two sets of dilators. With reference to FIG. 7 the Jamshidi like needle includes an inner stylet 32 and a cannula 34. The inner stylet 32 is initially situated within the cannula 34 and the two components are locked together via a handle 36. The working tip 38 of the inner stylet 32 extends beyond the cannula 34 and is configured to penetrate into bone to form a pilot hole. The inner stylet 32 may be unlocked and removed from the cannula 34 which remains in place in the pilot hole. A K-wire or similar guide structure may then be passed through the cannula 34 and into the pilot hole.

FIG. 8 depicts the first dilator set 40 which is used for dilating through the ilium 10 to form an access hole 28 through the ilium. The first dilator set 40 includes an initial dilator 42 and at least one supplemental dilator 44. The dilators 42 and 44 of the first set are advanced, sequentially one over the other, into the iliac crest 10 until an access hole 28 of the appropriate size is created. The first of the at least one supplemental dilators 44 is advanced over the initial dilator 42 and any remaining supplemental dilators 44 are advanced in sequence over the outer dilator. The initial dilator 42 may be guided over a K-wire 46 or similar guide (e.g. Steinman pin, etc. . . . ). The dilators of the first dilator set 40 are preferably made of a rigid material such as metal (e.g. stainless steel, aluminum, etc. . . . ) or impact resistant plastic (e.g. polycarbonate, etc. . . . ) that can be impacted through the bone of the iliac crest 10.

The second dilator set 48, illustrated in FIG. 9, is used for dilating through the iliac space 14 to the L5/S1 disc 12. The second dilator set 48 includes an initial dilator 50 and at least one supplemental dilator 52. The dilators 50 and 52 of the second set are advanced, sequentially one over the other, through the access hole 28 in the iliac crest 10 to the L5/S1 disc 12. To accomplish this safely, at least the initial dilator 50, and preferably the supplemental dilators 52 of the second dilator set 48 can be linked to a neurophysiology monitoring system. The dilators 50, 52 include an insulated body 54 with a stimulation electrode 56 at the distal end 58 and an attachment point 60 (for connecting to the neurophysiology system, for example, via a clip or other suitable connector) at the proximal end 62. The dilators 50, 52 may be made of a conductive material coated with an insulating material or they may be made of a non-conductive material with a conductive lead extending between the attachment point 60 and the stimulation electrode 56. The dilators of the second dilator set 48 are advanced, sequentially one over the other, through the iliac crest 10 to the L5/S1 disc 12 while stimulation signals are delivered to the surrounding tissue through the stimulation electrode 56 to detect the presence (and optionally the direction) of nerves, and particularly the L5 nerve root 16 near the distal end. While two different dilator sets are described, it should be appreciated that two different sets of dilators are not necessarily required, provided that the both functions (i.e. impaction through bone and nerve monitoring) may be completed with the dilators chosen.

Figure 10:
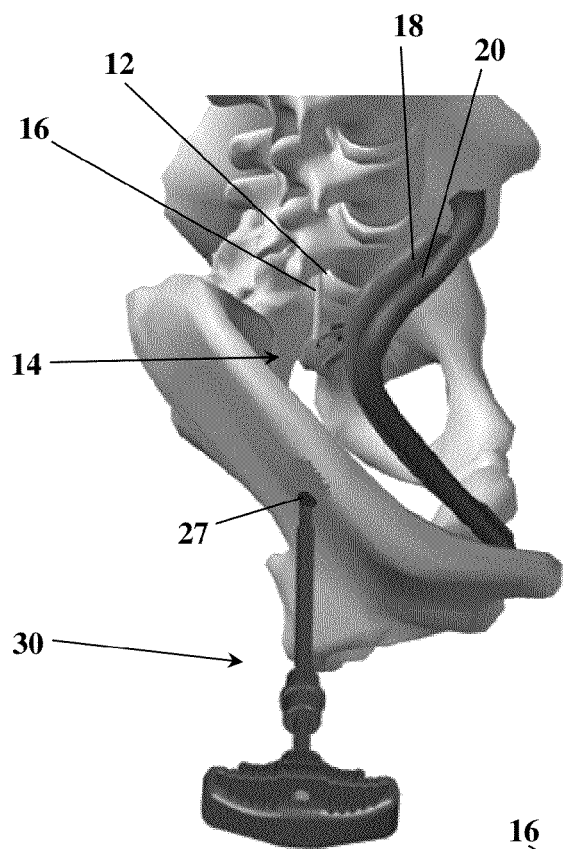
FIGS. 10-19 are lateral perspective views of the iliac space depicting certain steps carried out during an example method for forming a trans-iliac access corridor to the lateral aspect of the L5/S1 disc space, according to one example embodiment.

With reference to FIG. 10 and according to the example method described, with the patient preferably in a lateral decubitus position, the jamshidi needle 30 is first advanced to the appropriate entry point on the ilium 10 and docked in position. The entry point should be on the lateral surface of the ilium 10 and generally centered over the l5/S1 disc 12, which can be confirmed with a lateral fluoroscopy image. With the position confirmed the jamshidi 30 is advanced through the ilium 10 to form an initial pilot hole 27. The inner stylet 32 is removed and a k-wire 46 or similar guide is advanced through the jamshidi cannula 34 and the cannula 34 is removed leaving the k-wire to serve as a guide for the first dilator set 40. In an alternative step, the initial pilot hole 27 can be formed directly with a guide member of sufficient rigidity (e.g. Steinman pin) or the initial dilator 42.

Figure 11:
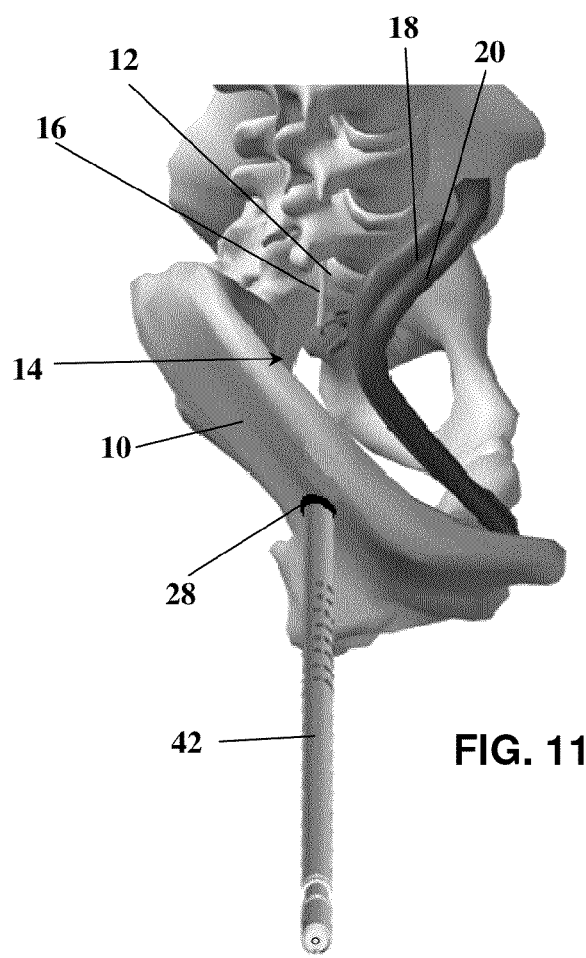
Figure 12:
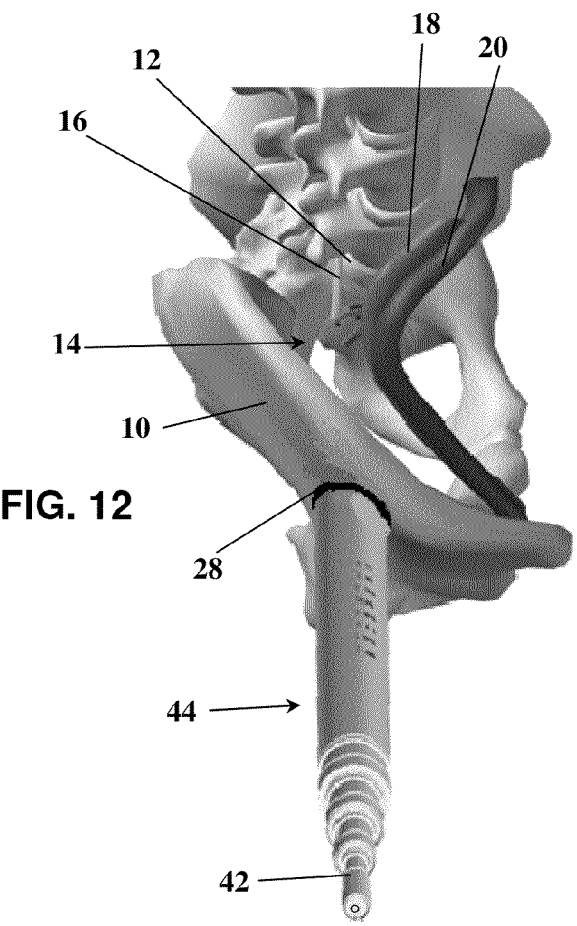
Figure 13:
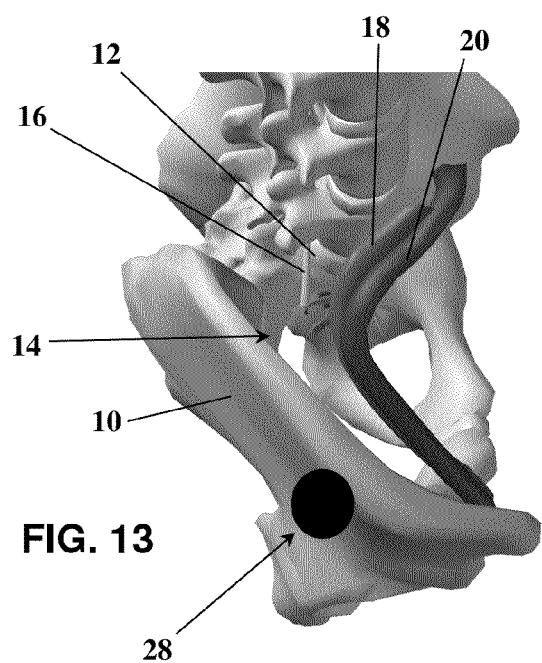

With the K-wire 46 (or other guide member) in place, the initial dilator 42 of the first dilator set 40 (impaction dilators) is advanced into the pilot hole, over the K-wire, as depicted in FIG. 11. The K-wire 42 is removed and the initial dilator 42 is impacted through the ilium 10, to form the access hole 28. After impaction, wagging of the dilator 42 (e.g. moving the dilator around in a conical motion) may be done to further increase the size of the access hole 28 prior to inserting the supplemental dilator(s) 44. Turning to FIG. 12, each of the supplemental dilators 44 are advanced in turn over the previous dilator and impacted through the ilium, increasing the size of the access hole 28 with each new dilator 44. As with the initial dilator 42, wagging of the dilator(s) 44 can be done to help increase the hole 28 size and facilitate easier insertion of the subsequent dilator 44. According to the example method described, three supplemental dilators 44 (for a total of four dilators in the first dilator set 40) are used, as pictured in FIG. 12. However, the number of dilators 44 and size of the access hole 28 may vary between patients and may depend on the size of the safe zone (determined during pre-operative planning). With the access hole 28 through the ilium 10 expanded to its final size, the first dilator set 40 is removed making way for insertion of the second dilator set 48 through the iliac space 14 to the L5/S1 disc (FIG. 13).

Figure 14:
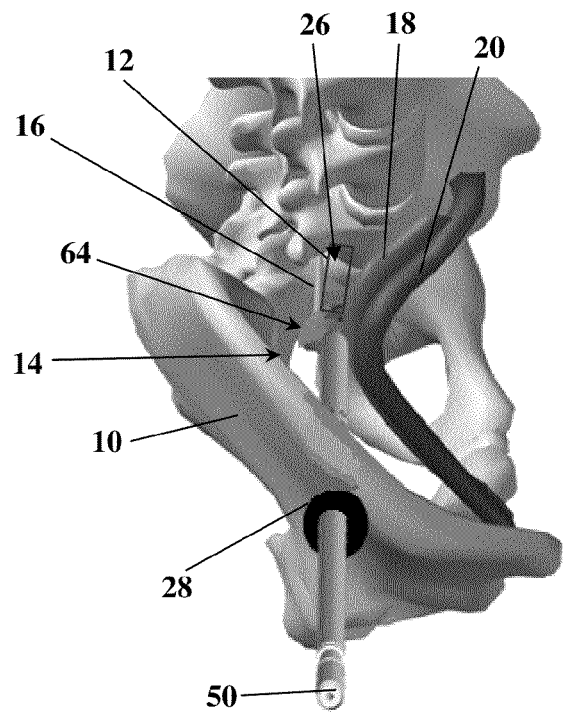

Turning to FIG. 14, the initial dilator 50 of the second dilator set 48 is advanced into the iliac space 14 through the access hole 28. In order to safely target the safe zone 26 the initial dilator 50 is connected to a neurophysiology monitoring system (not shown) to perform nerve detection as the dilator 50 is through the iliac space 14. As will now be described, the neurophysiology system is used to detect presence of nerves in the path of the initial dilator 50 and to direct the distal end of the initial dilator 50 towards the L5 nerve root. The neurophysiology system detects the presence of nerves by delivering electrical stimulation signals 64 of known currents through the stimulation electrode 56 on the distal end of the dilator 50 and monitoring for neuromuscular responses from muscles innervated by the nerves. The stimulation current amplitude required to elicit a response (i.e. stimulation threshold) is determined which provides an indication of nerve proximity (and optionally, direction) to the distal end of the dilator 50. The higher the stimulation threshold the farther away the nerve is, and vice versa. The threshold determination is performed repeatedly during advancement of the initial dilator 50 to continually update the proximity (and optionally directionality) indication.

Figure 15:
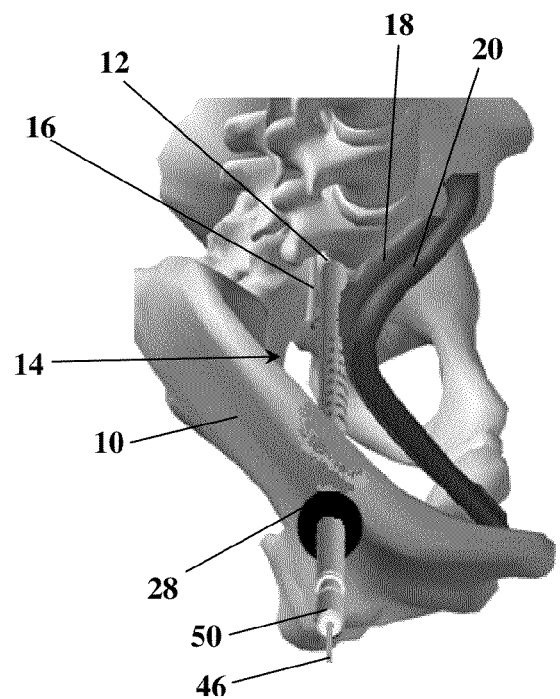

To ensure the second dilator set 48 is passed through the safe zone, the surgeon first directs the initial dilator 50 towards the L5 nerve root 16, which marks the posterior border of the safe zone. To seek out the L5 nerve root 16 the surgeon advances the initial dilator 50 such that the stimulation threshold gets lower and lower (indicating that the dilator is getting closer to the nerve root) until the threshold drops below a certain level, for example, 3 mA. When the stimulation threshold drops to this predetermined level, the surgeon knows that the distal end of the dilator 50 is indicating that the instrument is next to, but not contacting the nerve root 16. The goal at this stage is to position the dilator 50 right next to the nerve root 16 without injuring the root and keeping the dilator 50 anterior to the nerve root. Directionality may be determined (for example, by rotating the dilator to determine the direction that gives the lowest stimulation threshold) to ensure that the instrument is anterior to the nerve. With the location of the L5 nerve root 16 now known, the position of the iliac vein 18 is also known based on the information gained from the preoperative pre-operative planning. That is, the distance between the nerve root 16 and the iliac vein 18 is determined during pre-operative planning such that with the dilator 50 positioned right next to the nerve root 16, the surgeon knows how much room there is to work anterior to the nerve root 16 before encroaching on the iliac vein 18 (and iliac artery 20). Using this information, the initial dilator 50 is adjusted anteriorly into the safe zone to provide room relative to the L5 nerve root 16 for advancement of the supplemental dilator(s) 52, and is then docked on the L5/S1 disc 12 with a k-wire 46 to hold the position of the second dilator set 48 (FIG. 15) and prevent unwanted movement during dilation.

Figure 16:
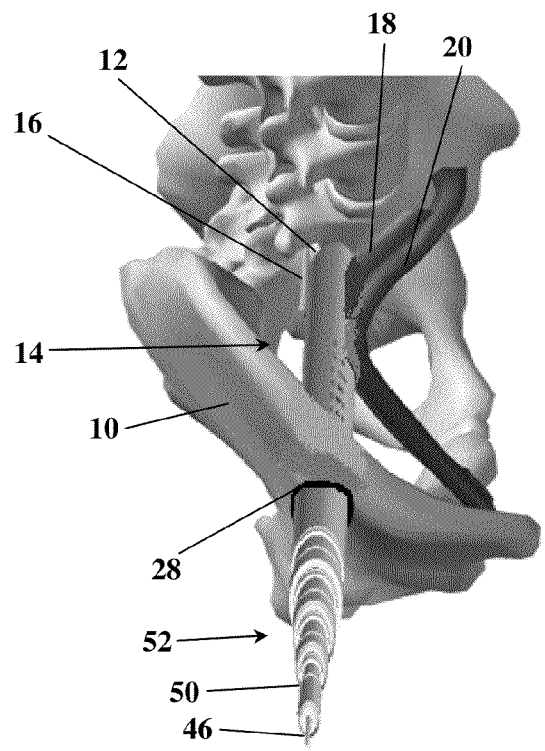
Figure 17:
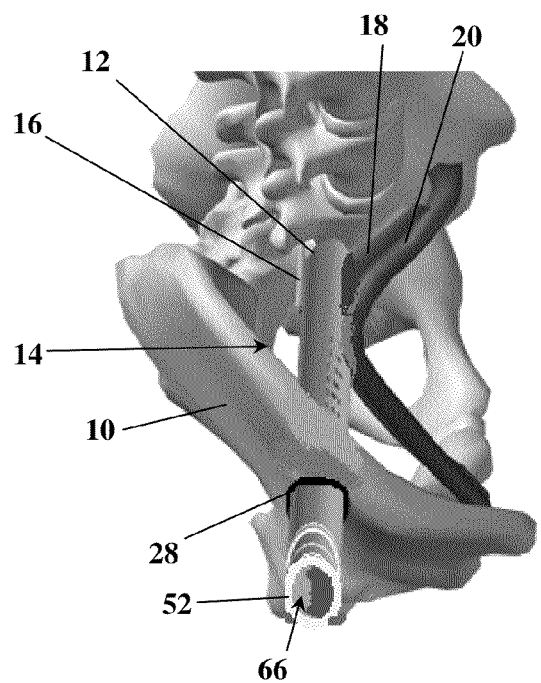

As illustrated in FIG. 16, the supplemental dilators 52 of the second dilator set 48 are then advanced in turn through the safe zone onto the disc space. Preferably, advancement of each of the supplemental dilators 52 is carried out with neurophysiology monitoring to maintain the safe relationship with the L5 nerve root 16. In addition, fluoroscopy may also be used to verify the position of the dilators in the safe zone 26. The outermost dilator is fixed in position (e.g. by penetrating into the disc or vertebral body, or, with a table mount) and the inner dilators are removed, leaving the outermost dilator 52 to define a protected working corridor 66 through which the L5/S1 disc can be accessed and operated on, as illustrated in FIG. 17. The size of the outermost dilator, and thus the size of the operative corridor, may be determined based on the size of the safe zone.

Figure 18:
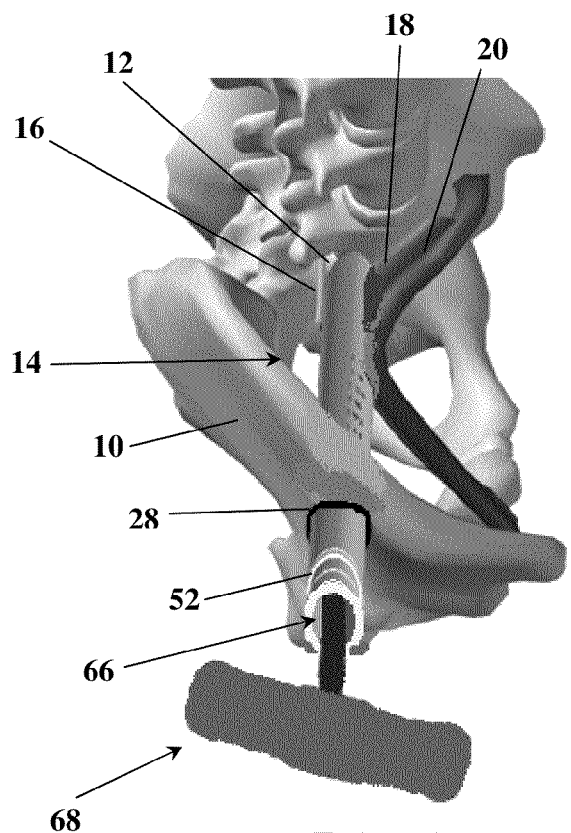
Figure 19:
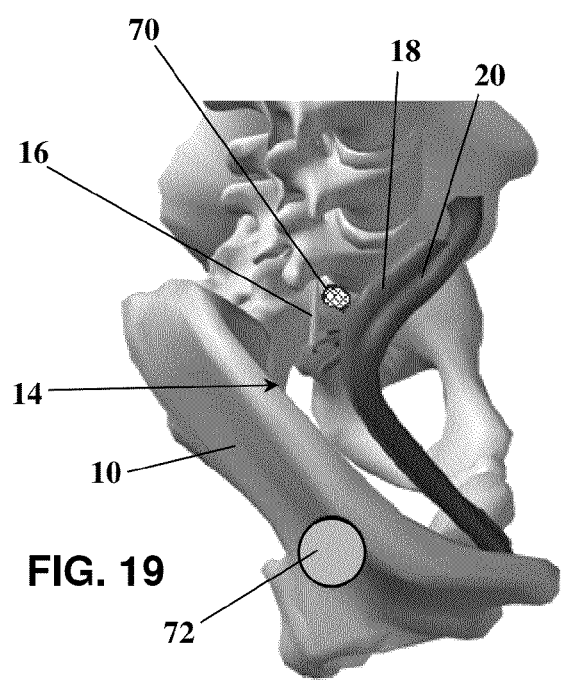

With reference to FIG. 18, the working corridor 66 provides a protected passage through which instruments 68 may be passed to perform the desired procedure on the L5/S1 disc. For example, the instruments may be curettes, reamers, shavers, etc. . . . for performing a discectomy. The instruments 68 may also be implant inserters for introducing implants which may also be deposited in the disc space to facilitate fusion or disc replacement. The implant may be a collapsible bag that is advanced through the working corridor in a collapsed configuration and then filled with a filler material in situ. The filler material may be a bone growth promoting material (e.g. bone chips, synthetic or cellular bone matrix, etc. . . . ). The implant may also be an expandable implant that is implanted into the disc space in a first smaller configuration and then expanded via any number of suitable expansion mechanisms. According to one example, the expandable implant is a collapsible textile bag with structural supports formed at the corners. The structural supports may be solid blocks (e.g. PEEK blocks) molded or otherwise adhered to bag in the corners. The implant may also be a single insert (e.g. PEEK block) dimensioned to be passed through the working corridor 66 and to extend across the L5/S1 disc space. The implant may also be a modular implant that is inserted through the working corridor 66 in several smaller pieces and assembled in the disc space 12 to form a larger implant. Bone growth promoting material may be packed in or around any of the implants described. Once work on the repaired L5/S1 disc 70 is complete, the final dilator 52 forming the working corridor 66 is removed and the wound closed. Though not necessary, the access hole 28 may be filled with bone graft 72 to promote bone growth and ultimately, the closure of the access hole (FIG. 19).

As evident from the above discussion and drawings, the apparatus and methods described accomplish the goals of gaining access to the 5/1 disc space in a fashion less invasive than traditional "open" surgeries, while still achieving significant disc preparation. And while the apparatus and methods have been described in terms of a best mode for achieving these objectives, it will be appreciated by those skilled in the art that variations may be accomplished in view of these teachings without deviating from the spirit or scope of the invention.

What is claimed is:

1. A method for accessing the L5/S1 disc of the lumbosacral junction, comprising the steps of:
    creating an access hole through the ilium;
    advancing an initial dilator through the access hole and towards the L5/S1 disc while and electrical stimulation signal is delivered from a stimulation electrode on the distal end of the initial dilator;
    assessing the neuromuscular response to the stimulation signal to indicate the proximity of the L5/S1 nerve root to the distal end of the initial dilator;
    directing the distal end of the dilator closer to the L5/S1 nerve root until the neuromuscular response indicates that the distal end of the initial dilator is next to but not contacting the L5 nerve root;
    advancing the distal end of the initial dilator through a safe zone between the L5 nerve root and the iliac vein to the L5/S1 disc; and
    advancing at least one supplemental dilator over the initial dilator through the access hole and safe zone to the L5/S1 disc; and
    removing all but the outermost dilator.

2. The method of claim 1, comprising the additional step of adjusting the position of the initial dilator anteriorly to the center of the safe zone.

3. The method of claim 2, comprising the additional step of docking the initial dilator to the spine by advancing a K-wire through the initial dilator and penetrating the annulus of the L5/S1 disc.

4. The method of claim 3, wherein three supplemental dilators are advanced over the initial dilator the access hole and safe zone to the L5/S1 disc.

5. The method of claim 1, wherein while advancing the at least one supplemental dilator an electrical stimulation signal is delivered from a stimulation electrode on the distal end of the at least one supplemental dilator to detect nerve proximity during advancement of the at least one supplemental dilator to the L5/S1 disc.

6. The method of claim 1, comprising the additional step of performing a procedure on the L5/S1 disc through a passageway in the outermost dilator.

7. The method of claim 6, wherein the procedure performed on the L5/S1 disc is a discectomy.

8. The method of claim 7, where the procedure performed on the L5/S1 disc further includes a fusion.

9. The method of claim 8, wherein the fusion procedure includes implanting a fusion implant in the L5/S1 disc space through the passageway in the outermost dilator.

10. The method of claim 9, wherein the fusion implant include an expandable textile bag that is inserted in a deflated stated and expanded within the L5/S1 disc space by introducing bone growth promoting materials into the bag.

11. The method of claim 10, wherein the textile bag includes integrated structural supports.

12. The method of claim 11, wherein the integrated structural supports are comprised of polymer blocks attached to the corners of the textile bag.

13. The method of claim 8, wherein the fusion implant is a single insert dimensioned to extend across the L5/S1 disc space.

14. The method of claim 13, wherein the single insert includes a fusion aperture extending from a top surface to a bottom surface that is packed with bone growth promoting materials prior to introduction of the implant.

15. The method of claim 1, wherein the step of creating the access hole through the ilium comprises:
   advancing an instrument into the ilium and forming a pilot hole;
   advancing an initial dilator into the pilot hole and impacting the dilator through the ilium to create an access hole; and
   advancing at least one supplemental dilator over the initial dilator and impacting the dilator through the ilium to enlarge the access hole.

16. The method of claim 15, wherein the instrument advanced into the ilium to form the pilot hole is a jamshidi needle.

17. The method of claim 16, comprising the additional steps of:
   removing an inner stylet from a cannula of the jamshidi needle;
   introducing a K-wire through the cannula;
   removing the cannula; and
   introducing the initial dilator into the pilot hole over the K-wire.

18. The method of claim 15, wherein the instrument advanced to the ilium to form the pilot hole is a Steinman pin.

19. The method of claim 15, wherein three supplemental dilators are advanced over the initial dilator and impacted through the ilium to enlarge the access hole.

20. The method of claim 1, wherein the outermost dilator is anchored in position prior to removing the remaining dilators.

* * * * *